(12) United States Patent
Muniglia et al.

(10) Patent No.: US 8,679,794 B2
(45) Date of Patent: Mar. 25, 2014

(54) ENZYME METHOD OF EXTRACTING OILS AND PROTEINS FROM VEGETABLE MATTER IN AN AQUEOUS MEDIUM

(75) Inventors: Lionel Muniglia, Jevoncourt (FR); Michel Girardin, Nancy (FR); Bernadette Piffaut, Villiers les Nancy (FR); Guillaume Ricochon, Moussey (FR)

(73) Assignee: Universite de Lorraine, Nancy (FR)

( * ) Notice: Subject to any disclaimer, the term of this patent is extended or adjusted under 35 U.S.C. 154(b) by 0 days.

(21) Appl. No.: 13/501,162

(22) PCT Filed: Oct. 14, 2010

(86) PCT No.: PCT/EP2010/065447
§ 371 (c)(1),
(2), (4) Date: Apr. 10, 2012

(87) PCT Pub. No.: WO2011/045387
PCT Pub. Date: Apr. 21, 2011

(65) Prior Publication Data
US 2012/0196332 A1  Aug. 2, 2012

(30) Foreign Application Priority Data

Oct. 16, 2009  (FR) ..................................... 09 57274

(51) Int. Cl.
*C12P 19/14* (2006.01)
(52) U.S. Cl.
USPC .............................. 435/99; 435/209; 435/267
(58) Field of Classification Search
None
See application file for complete search history.

(56) References Cited

U.S. PATENT DOCUMENTS

| 4,904,483 A | 2/1990 | Christensen et al. |
| 6,433,146 B1 * | 8/2002 | Cheryan ..................... 530/373 |
| 6,500,973 B2 * | 12/2002 | Fontenot ......................... 554/70 |
| 2009/0215127 A1 * | 8/2009 | Breneman et al. .............. 435/95 |

FOREIGN PATENT DOCUMENTS

| EP | 0 113 165 A1 | 7/1984 |
| EP | 1 658 360 B1 | 5/2007 |
| WO | 01/60182 A1 | 8/2001 |
| WO | 03/028473 A1 | 4/2003 |

OTHER PUBLICATIONS

Rosenthal et al. "Aqueous and enzymatic processes for edible oil extraction." (1996) Enzyme and Microbial Technology, 19:402-420.*
Spagnuolo et al. "Synergistic Effects of Cellulolytic and Pectinolytic Enzymes in Degrading Sugar Beet Pulp." (1997) Bioresource Technology, 60:215-222.*
Gilbert and Hazlewood "Bacterial cellulases and xylanases." (1993) Journal of General Microbiology, 139:187-194.*
Gonzalez and Rosso "Determination of pectin methylesterase activity in commercial pectinases and study of the inactivation of kinetics through two potentiometric procedures" (2011) Ciencia e Technologia de Alimentos, 31:412-417.*
Bouzid et al. "Fungal enzymes as a powerful tool to release simple phenolic compounds from oil oil by-product." (2005) Process Biochemistry 40:1855-1862.*
Stamenkovic et al. "The effect of agitation intensity on alkali-catalyzed methanolysis of sunflower oil" (2007) Bioresource Technology 98:2688-2699.*
Ohlsen, "Modern Processing of Rapeseed" (1992) Journal of the American Oil Chemists' Society, vol. 69: 195-198.*
Xu et al. "Functional Properties of Chinese Rapeseed Protein Isolates" (1994) Journal of Food Science vol. 59: 1127-1130.*
Dev et al. "Functional Properties of Rapeseed Protein Products with Varying Phytic Acid Contents" (1986) Journal of Agricultural Food Chemistry vol. 34: 775-780.*
Sengupta R et al.: "Enzymatic Extraction of Mustard Seed and Rice Bran", Journal of the American Oil Chemists' Society, Springer, Berlin, DE, vol. 73, No. 6, Jan. 1, 1996, pp. 687-692.
Juhasz T et al.: "Characterization of cellulases and hemicellulases produced by *Trichoderma reesei* on various carbon sources", Process Biochemistry, Elsevier, NL, vol. 40, No. 11, Nov. 1, 2005, pp. 3519-3525.
Donaghy J A et al.: "Novel screening assay for the detection of phenolic acid esterases", World Journal of Microbiology and Biotechnology, vol. 10, No. 1, 1994, pp. 41-44.
Karlovic D J et al.: "Corn germ oil extraction by a new enzymatic process", ACTA Alimentaria. Akademiai Krado, Budapest, HU, vol. 23, No. 4, Jan. 1, 1994, pp. 389-400.
Shao Bing Zhang et al.: "Optimization of the aqueous enzymatic extraction of rapeseed oil and protein hydrolysates.", Journal of the American Oil Chemists' Society, vol. 84, No. I, Jan. 1, 2007, pp. 97-105.

(Continued)

*Primary Examiner* — Jon P Weber
*Assistant Examiner* — Teresa E Knight
(74) *Attorney, Agent, or Firm* — Young & Thompson

(57) ABSTRACT

Method for extracting oils, proteins and fermentable sugars from vegetable material in an aqueous medium, includes:
  a) adding water to the vegetable material;
  b) adding an enzyme mixture containing at least one cellulase, at least one hemicellulase, and at least one pectinase, the ratio between the pectinase activity and the cellulase activity being at least 0.14, and the ratio between the pectinase activity and the hemicellulase activity being at least $7.10^{-3}$, the pectinase activity being less than 120 μmol/min/mL;
  c) incubating the vegetable material and the enzyme mixture with stirring to release oils, proteins and fermentable sugars in the reaction medium;
  d) separating the reaction medium to obtain free oil, an aqueous phase containing proteins and fermentable sugars, and a solid phase;
  e) optionally separating and recycling an emulsion of free oil or aqueous phase, to the medium;
  f) separating the proteins and fermentable sugars from the aqueous phase.

16 Claims, No Drawings

(56) References Cited

OTHER PUBLICATIONS

Ramadan M F et al.: "Oil extractability from enzymatically treated goldenberry (*Physalis peruviana* L.) pomace: range of operational variables.", International Journal of Food Science & Technology, vol. 44, No. 3, Mar. 1, 2009, pp. 435-444.
Picuric-Jovanovic K et al.: "Aqueous-enzymatic extraction of plum kernel oil.", FETT/LIPID, vol. 99, No. 12, Dec. 1, 1997, pp. 433-435.
Database FSTA [Online] International Food Information Service (IFIS), Frankfurt-Main, DE; 1994, Karlovic 0 J et al: "Corn germ oil extraction by a new enzymatic process." Database accession No. FS-1995-10-N-0053 abstract, & ACTA Alimentaria, vol. 23, No. 4, 1994, pp. 389-400.
French Search Report, dated Jun. 29, 2010, from corresponding French application.
International Search Report, dated Mar. 14, 2011, from corresponding PCT application.

\* cited by examiner

ENZYME METHOD OF EXTRACTING OILS AND PROTEINS FROM VEGETABLE MATTER IN AN AQUEOUS MEDIUM

TECHNICAL FIELD

The present invention relates to an enzyme method for extracting in an aqueous medium, oils, proteins and fermentable sugars from vegetable material.

STATE OF THE ART

Traditional methods for extracting oils involve organic solvents such as hexane. The use of these solvents causes many safety problems for the installations and personnels, for human health and problems of preservation of the environment. Indeed it is sought to reduce the emissions of volatile organic compounds (VOCs).

Since about thirty years, several research teams worldwide have been working towards the development of "clean" extraction methods for-oil seeds. These methods are based on extraction of oils via an aqueous route combining enzymes and biological catalysts. These methods, although intended to be ecological, nevertheless provide the use of a solvent or provide a step for correcting the pH with alkaline or acid compounds, these methods have not been validated on an industrial scale since the catalysts used do not allow good yields at such a scale.

The object of the present invention is to propose a novel method for extracting oils from a vegetable material, without the drawbacks listed above. More particularly, the object of the present invention is to propose a method for extracting vegetable oils with which it is possible to suppress the use of all organic solvents and obtain a clean method allowing extraction of oils, proteins and other co-products with high nutritional properties.

The object of the present invention is also to propose a method which may be applied industrially with interesting yields.

The object of the present invention is also to propose a method with which all the extracted products stemming from this method may be used.

DISCLOSURE OF THE INVENTION

For this purpose, the present invention relates to an enzyme method for extracting in an aqueous medium, oils, proteins and fermentable sugars from vegetable material, comprising the following steps:
a) adding water to the vegetable material having a suitable particle size,
b) adding an enzyme mixture containing at least one cellulase, at least one hemicellulase and at least one pectinase, the ratio between the activity of the pectinase and the activity of the cellulase being of at least 0.14, preferably comprised between 0.3 and 2.5, and more preferentially between 0.35 and 0.45, and the ratio between the activity of the pectinase and the activity of the hemicellulase being of at least $7.10^{-3}$; preferably comprised between $1.10^{-2}$ and 0.5, and more preferentially between $1.10^{-2}$ and $2.10^{-2}$, the activity of the pectinase being less than 120 μmol/min/mL, and preferably less than 100 μmol/min/mL,
c) incubating vegetable material and enzyme mixture with stirring in order to release from the reaction medium oils, proteins and fermentable sugars, for a duration depending on the sought yields,
d) separating the reaction medium in order to obtain free oil, an aqueous phase containing proteins and fermentable sugars and a solid phase,
e) optionally separating an emulsion of the free oil or of the aqueous phase, and recycling the emulsion in the reaction medium,
f) separating the proteins and fermentable sugars from the aqueous phase.

The present invention also relates to the use, in a method as defined above, of an enzyme mixture as defined above, for suppressing any step for correcting the pH in said method.

EMBODIMENT(S) OF THE INVENTION

According to the invention, the enzyme method for extracting in an aqueous medium, oils, proteins and fermentable sugars from vegetable material, comprises the following steps:
a) adding water to the vegetable material having a suitable particle size,
b) adding an enzyme mixture containing at least one cellulase, at least one hemicellulase and at least one pectinase, the ratio between the activity of the pectinase and the activity of the cellulase being of at lease 0.14, and the ratio between the activity of the pectinase and the activity of the hemicellulase being of at least $7.10^{-3}$, the activity of the pectinase being non-zero and less than 120 μmol/min/mL,
c) incubating the vegetable material and the enzyme mixture with stirring for releasing into the reaction medium, oils, proteins and fermentable sugars, for a duration depending on the sought yields,
d) separating the reaction medium in order to obtain free oil, an aqueous phase containing proteins and fermentable sugars, and a solid phase,
e) optionally separating an emulsion of the free oil or of the aqueous phase, and recycling the emulsion into the reaction medium,
f) separating the proteins and/or fermentable sugars from the aqueous phase, depending on the products which are desirably recovered.

As regards step a), the suitable particle size of the vegetable material is advantageously obtained by milling said vegetable material. The milling may be as fine as possible for promoting the action of the enzymes. Ideally, all the particles should have a size close to 50 μm, preferably close to 10 μm.

Advantageously, the volume of water is minimized so as to reduce the effluents to be treated and to concentrate the extracted products. Preferably, the mass of water added to the vegetable material is equal to 1 to 2 times the mass of said vegetable material and does not exceed this amount.

Preferably, the method according to the invention further comprises, after step a), a step for deactivation of the endogenous enzymes of the water/vegetable material mixture. This deactivation is preferably accomplished with heat. The water/vegetable material mixture is heated to a temperature comprised between 80° C. and 105° C. for 5 to 20 mins. The temperature is then brought back to the temperature used for step b).

As regards step b), the ratio between the activity of the pectinase and the activity of the cellulase is preferably comprised between 0.3 and 2.5, and more preferentially between 0.35 and 0.45, and the ratio between the activity of the pectinase and the activity of the hemicellulase is preferably comprised between $1.10^{-2}$ and 0.5, and more preferentially between $1.10^{-2}$ and $2.10^{-2}$, the activity of the pectinase preferably being less than 100 μmol/min/mL.

More particularly, the enzyme mixture used contains the enzyme activities in the following proportions:
cellulases:
- betaglucosidase: between 1 μmol/min/mL and 30 μmol/min/mL, preferably between 4.5 μmol/min/mL and 13 μmol/min/mL,
- endocellulase: between 20 μmol/min/mL and 200 μmol/min/mL, preferably between 27 μmol/min/mL and 120 μmol/min/mL,
- exocellulase: between 0 and 50 μmol/min/mL, preferably between 9 μmol/min/mL and 25.5 μmol/min/mL, hemicellulases:
- arabinanase: between 300 μmol/min/mL and 2,000 μmol/min/mL, preferably between 465 μmol/min/mL and 1,335 μmol/min/mL,
- xylanase: between 0 and 2,000 μmol/min/mL, preferably between 300 μmol/min/mL and 1,700 μmol/min/mL,
- galactanase: between 300 μmol/min/m: and 2,000 μmol/min/mL, preferably between 750 μmol/min/m: and 1,000 μmol/min/mL, pectinases:
- endopolygalacturonase: between 40 μmol/min/mL and 120 μmol/min/mL, preferably between 61 μmol/min/mL and 86 μmol/min/mL,
- pectin methylesterase: between 1 μmol/min/mL and 20 μmol/min/mL, preferably between 1 μmol/min/mL: and 5 μmol/min/mL.

These enzymes are commercially available.

In the particular case when the vegetable material is rapeseed, the enzyme mixture used may contain enzyme activities in the following proportions:
cellulases:
- betaglucosidase: between 3 μmol/min/mL and 6 μmol/min/mL,
- endocellulase: between 110 μmol/min/mL and 130 μmol/min/mL,
- exocellulase: between 20 μmol/min/mL and 30 μmol/min/mL, hemicellulases:
- arabinanase: between 1,200 μmol/min/mL and 1,500 μmol/min/mL,
- xylanase: between 1,500 μmol/min/mL and 2,000 μmol/min/mL,
- galactanase: between 800 μmol/min/mL and 1,200 μmol/min/mL, pectinases:
- endopolygalacturonase: between 50 μmol/min/mL and 70 μmol/min/mL,
- pectin methylesterase: between 1 μmol/min/mL: and 20 μmol/min/mL.

In the particular case when the vegetable material is sunflower, the enzyme mixture used may contain enzyme activities in the following proportions:
cellulases:
- betaglucosidase: between 11 μmol/min/mL and 14 μmol/min/mL,
- endocellulase: between 25 μmol/min/mL and 35 μmol/min/mL,
- exocellulase: between 8 μmol/min/mL and 12 μmol/min/mL, hemicellulases:
- arabinanase: between 450 μmol/min/mL and 550 μmol/min/mL,
- xylanase: between 0 and 300 μmol/min/mL,
- galactanase: between 700 μmol/min/mL and 900 μmol/min/mL, pectinases:
- endopolygalacturonase: between 75 μmol/min/mL and 95 μmol/min/mL,
- pectin methylesterase: between 1 μmol/min/mL and 5 μmol/min/mL.

Preferably, the amounts used of the enzyme mixture is as defined above and is comprised between 0.25% and 10%, preferably between 1% and 6%, by volume of the water/vegetable material mixture.

Further, the enzyme mixture may also comprise a phenolate esterase, preferably a ferulate esterase, the activity of which is comprised between 1 μmol/min/mL and 15 μmol/min/mL, preferably comprised between 4 μmol/min/mL and 15 μmol/min/mL, and preferably comprised between 7.5 μmol/min/mL and 15 μmol/min/mL in the particular case of rapeseed and between 4 μmol/min/mL and 6 μmol/min/mL in the particular case of sunflower.

Advantageously, the incubation according to step c) is carried out for 2 to 20 hours, preferably between 4 and 12 hours, at a temperature comprised between 25° C. and 75° C., preferably between 40° C. and 60° C., and preferably around 50° C.

Advantageously, no pH correction step is provided, in particular when the vegetable material treated is rapeseed or sunflower.

The pH of the reaction medium should be comprised between 5.5 and 4.5, and preferably comprised between 4.8 and 5.

However, it may be necessary in certain cases to correct the pH in order to correspond to the optimum pH of the enzymes. In this case, it is possible to use acids such as acetic acid (E 260) or citric acid (E 330).

The stirring provided in step c) is preferably carried out by means of a mixer comprising flat blades promoting mixing and limiting shearing. The stirring should be sufficient for ensuring heat transfer, but minimized in order to avoid the occurrence of an emulsion.

The incubation time is adapted depending on the desired amount of extracted products. Indeed, the release of oils, sugars and proteins will depend on the hydrolysis time. The majority of the proteins are very rapidly solubilized, for example within less than one hour. The oil yield is stabilized between 4 and 6 hours, and then it continues to increase more slowly. The concentration of fermentable sugars regularly increases up to 12 hours and beyond.

The hydrolysis reaction is then stopped by deactivating the enzymes by preferably heating between 80° C. and 105° C. for example, for 5 to 20 minutes.

Next the reaction medium is separated, according to step d) by using all the known suitable separation techniques, such as centrifugation or decantation. Ideally, this separation is carried out under 3,000 g for 5 minutes at 80° C.

Advantageously, the separation of the extracted products is achieved by means of a three-phase decanter (tricanter). Such a device is a horizontal centrifugal decanter for continuous separation of the reaction medium into three phases: the free oil, an aqueous phase containing a portion of the proteins and of the fermentable sugars, and a solid phase formed by partly de-oiled cakes, with the tricanter it is possible to recycle the materials and handle different hydrolysis times depending on the products which are desirably recovered.

Depending on the vegetable material, from which the oils are intended to be extracted, some emulsion may be formed in the oily phase or in the aqueous phase.

The enzyme mixture used in the invention gives the possibility of limiting the amount of emulsion, in particular for sunflower.

When some emulsion is formed, the latter is separated from the phase with which it was collected, for example by means of a decanter. The emulsion may be recycled and reinjected into the tricanter so as to be subject to fresh hydrolysis for releasing the oils which it contains.

In Table I below, are indicated the amounts of products obtained from 10 kg of seeds (with 50% oil) mixed with 10 kg of water, treated according to the method of the invention.

TABLE I

| Products | Amount from 10 kg of seeds and 10 kg of water |
|---|---|
| Oil | 4 to 4.7 kg |
| Aqueous phase and emulsion | 11 to 15 kg |
| Including sugars | 60 to 100 g/l of aqueous phase |
| Including proteins | 25 to 35 g/l of aqueous phase |
| Cakes (the remainder of the seeds) | 2-4 kg |

The recovered free oil is immediately stored under/with an inert gas, such as nitrogen, while awaiting its refining if necessary. It contains a large proportion of tocopherols. These sought antioxidants are conventionally carried away during the deodorization step. Their presence in great number in the oils extracted according to the method of the invention, ensures that the are partly preserved during the deodorization step.

The cakes are dried and stored or recycled in order to undergo a second hydrolysis. They may be used for feeding animals.

The fermentable sugars and the proteins contained in the aqueous phase are separated by any means allowing this, notably by filtration (nano-ultrafiltration) techniques or by precipitation techniques.

The fermentable sugars of the aqueous phase undergo fermentation by adapted microorganisms (bacteria, yeasts, fungi) such as *Saccharomyces cerevisiae*, in order to produce ethanol, which may be used as a biofuel.

The proteins are extracted in a significant way, the extraction yields being about 10 times greater than that of traditional extraction methods. The proteins are of very good properties, very little denaturated.

Thus, all the extracted products may be recovered.

Preferably, the method according to the invention is applied with the vegetable material selected from the group comprising fat cakes stemming from first pressing and oilseeds.

The oilseeds are preferably selected from the group comprising rapeseed and sunflower. The method according to the invention may also be applied to oilfruit, such as olives.

The following examples illustrate the present invention without however limiting the scope thereof.

EXAMPLES

Examples 1 to 5

750 grams of sunflower seeds are milled in a knife mill for 1 min 30s (3 times 30 seconds). The required volume of distilled water is added to the milled product, mixed and boiled in a microwave oven in order to deactivate the endogenous enzymes. The heating is stopped when boiling begins. In parallel, the enzyme mixture is made in a beaker. In order to avoid a thermal shock, the enzymes being stored at 4° C., the beaker is immersed in a water bath at room temperature. The water bath is then started with a set temperature value of 50° C. so that the enzymes experience a gradual rise in temperature. The milled seeds are poured into a fermenter of 2 L and temperature control and stirring are started. When the medium reaches 50° C., the enzyme mixture is added and the hydrolysis reaction begins. The pH is close to the optimum pH of the enzymes and does not require any correction. After 4 hours, the reaction medium is separated by means of a centrifuge at 9,000 g for 15 mins at 20° C. The different phases are recovered.

For the Examples 1, 3 and 4, the emulsion separated from the aqueous phase is not recycled.

For Example 2, the emulsion separated from the aqueous phase is recycled.

The oil mass percentage contained in each extracted fraction (free oil, aqueous phase+emulsion, solid phase) is measured relatively to the totality of the oils recovered in the three fractions (free oil/aqueous phase+emulsion/solid phase), without recycling the emulsion and with recycling of the emulsion.

As a comparative example, a batch of seeds is treated in the same way but without any enzyme (comparative Example 5).

The results are indicated in the following Table II:

TABLE II

| | Ex. 1 (inv.) | Ex. 2 (inv.) | Ex. 3 (inv.) | Ex. 4 (inv.) | Ex. 5 (comp.) |
|---|---|---|---|---|---|
| Time (h) | 4 | 4 + recycl. | 12 | 4 | 4 |
| Temperature (° C.) | 50 | 50 | 50 | 50 | 50 |
| Stirring (rpm) | 340 | 340 | 340 | 340 | 450 |
| pH | 5.2 | 5.1 | 4.9 | 5.1 | 5.5 |
| Seeds/water ratio | 0.9 | 0.9 | 0.9 | 0.9 | 0.9 |
| Enzyme/seed ratio | 0.05 | 0.05 | 0.05 | 0.05 | 0 |
| Betaglucosidase[a] | 12.7 | 12.7 | 12.7 | 20.2 | 0 |
| Endocellulase[a] | 27.1 | 27.1 | 27.1 | 10.3 | 0 |
| Exocellulase[a] | 9.4 | 9.4 | 9.4 | 0.7 | 0 |
| Arabinanase[a] | 468.6 | 468.6 | 468.6 | 3.4 | 0 |
| Xylanase[a] | 8.4 | 8.4 | 8.4 | 0 | 0 |
| Galactanase[a] | 775.8 | 775.8 | 775.8 | 153 | 0 |
| Endopolygalacturonase[a] | 85.1 | 85.1 | 85.1 | 76.9 | 0 |
| pectin methylesterase | 1.8 | 1.8 | 1.8 | 1.7 | 0 |
| Ferulate esterase | 3.8 | 3.8 | 3.8 | 4.2 | 0 |
| Free oil mass (g) | 270.3 | 335.7 | 329.4 | 278.7 | 127.9 |
| Emulsion oil mass (g) | 26.3 | 14.6 | 33.3 | 56.3 | 26.7 |
| Solid phase oil mass(g) | 56.5 | 32.18 | 35.6 | 72.7 | 197.0 |
| Total oil mass(g) | 353.1 | 383.2 | 398.3 | 407.8 | 351.6 |
| Free oil mass (%) | 76.5 | 87.6 | 82.7 | 68.5 | 36.4 |
| Emulsion oil mass (%) | 7.5 | 3.8 | 8.4 | 13.2 | 7.6 |
| Solid phase oil mass (%) | 16.0 | 8.4 | 9.0 | 17.3 | 56.0 |

[a]activity in µmol/min/mL

The method according to the invention gives the possibility of obtaining results close to those obtained by traditional industries using solvents. The obtained emulsion contains very little oil. As a comparison, there generally remains 4-5% of oil in the emulsion in traditional methods with solvent, and there remains 10-15% of oil in the emulsion in known methods without solvent, depending on the seeds.

The concentration of sugars varies from 40 to 90 g/l of aqueous phase, for a hydrolysis time from 4 to 12 hours.

Examples 6 to 12

The Examples 6 to 12 are treated in the same way as the examples above but on rapeseeds and without recycling the emulsion separated from the aqueous phase.

For Examples 6 and 7, the hydrolysis duration is 15 hours. Example 6 is free of any ferulate esterase activity.

As a comparative example, a batch of seeds is treated in the same way but without any enzyme (comparative Example 10) or with the same enzyme but with ratios between activities not being part of the invention.

The results are indicated in the following Table III:

TABLE III

|  | Ex. 6 (inv.) | Ex. 7 (inv.) | Ex. 8 (inv.) | Ex. 9 (inv.) | Ex. 10 (comp.) | Ex. 11 (comp.) | Ex. 12 (comp.) |
|---|---|---|---|---|---|---|---|
| Time (h) | 15 | 15 | 4 | 4 | 4 | 4 | 4 |
| Temperature (° C.) | 50 | 50 | 50 | 50 | 50 | 50 | 50 |
| Stirring | 300 | 300 | 300 | 300 | 450 | 300 | 330 |
| pH | 5.0 | 4.9 | 5.0 | 4.9 | 5.2 | 5.0 | 5.1 |
| Seed/water ratio | 0.67 | 0.67 | 0.67 | 0.67 | 0.67 | 0.67 | 0.67 |
| Enzyme/seed ratio | 0.05 | 0.05 | 0.05 | 0.05 | 0 | 0.05 | 0.05 |
| Betaglucosidase[a] | 8 | 8 | 8 | 4.7 | 0 | 1.39 | 24.3 |
| Endocellulase[a] | 14 | 14 | 14 | 119.8 | 0 | 218.2 | 35.8 |
| Exocellulase[a] | 2 | 2 | 2 | 25.3 | 0 | 29.2 | 13.0 |
| Arabinanase[a] | 10 | 10 | 10 | 1334.8 | 0 | 1511.1 | 697.0 |
| Xylanase[a] | 0 | 0 | 0 | 1713.9 | 0 | 4139.1 | 12.6 |
| Galactanase[a] | 450 | 450 | 450 | 1000.8 | 0 | 175.2 | 907.2 |
| Endopolygalacturonase[a] | 57.9 | 57.9 | 57.9 | 61.7 | 0 | 0 | 126.62 |
| Pectin methylesterase[a] | 3.5 | 3.5 | 3.5 | 0.3 | 0 | 0 | 0.95 |
| Ferulate esterase[a] | 0 | 27 | 27 | 6.5 | 0 | 6.5 | 3.8 |
| Free oil mass(g) | 180.9 | 202.0 | 51.7 | 118.8 | 15.0 | 91.4 | 70.0 |
| Emulsion oil mass(g) | 58.5 | 45.7 | 176.53 | 114.0 | 188.8 | 114.5 | 158.9 |
| Solid phase oil mass (g) | 44.3 | 39.4 | 66.42 | 63.67 | 95.9 | 98.4 | 101.1 |
| Total oil mass(g) | 284 | 287.3 | 295.2 | 296.6 | 299.7 | 304.6 | 330.1 |
| Free oil mass (%) | 63.7 | 70.3 | 17.5 | 40.1 | 5 | 30 | 21.2 |
| Emulsion oil mass (%) | 20.6 | 15.9 | 59.8 | 38.4 | 63 | 37.6 | 48.1 |
| Solid phase oil mass (%) | 15.6 | 13.7 | 22.5 | 21.5 | 32 | 32.3 | 30.6 |

[a]activity µmol/min/mL

Examples 6 to 9 show the role of ferulate esterase.

Example 9 with a duration of 4 hours shows the role of the hydrolysis time, just as with Examples 7 and 8 made with the same enzyme mixture, but with a different hydrolysis duration.

The concentrations of sugars vary from 40 to 90 g/l of aqueous phase for a hydrolysis time from 4 to 12 hours.

The concentration of proteins are from 30 to 35 g/l of aqueous phase as soon as the first hydrolysis hour.

The comparative examples 10 to 12 show the advantages of the activity ratios of the enzyme mixtures used in the method of the invention as compared with methods without any enzyme or using enzyme mixtures having different activity ratios from those of the present invention. In particular, the method using enzyme mixtures according to the invention gives the possibility of obtaining a larger mass of free oil than the methods using enzyme mixtures having activity ratios different from those of the present invention.

The invention claimed is:

1. An enzyme method for extraction in an aqueous medium, oils, proteins and fermentable sugars from vegetable material, comprising the following steps:
   a) adding water to the vegetable material having a suitable particle size,
   b) adding an enzyme mixture containing at least one cellulose, at least one hemicellulose, and at least one pectinase, the ratio between the pectinase activity and the cellulose activity being at least 0.14, the ratio between the pectinase activity and the hemicellulose activity being between $1 \times 10^{-2}$ and 0.5, and the pectinase activity being less than 120 µmol/min/mL,
   c) incubating the vegetable material and the enzyme mixture with stirring in order to release in the reaction medium oils, proteins and fermentable sugars, for a duration depending on the sought yields,
   d) separating the reaction medium in order to obtain free oil, an aqueous phase containing proteins and fermentable sugars, and a solid phase,
   e) optionally separating an emulsion of the free oil or of the aqueous phase, and recycling the emulsion in the reaction medium,
   f) separating the proteins and fermentable sugars from the aqueous phase.

2. The method according to claim 1, wherein the suitable particle size of the vegetable material is obtained by milling said vegetable material.

3. The method according to claim 1, wherein the mass of water added to the vegetable material is equal to 1 to 2 times the mass of said vegetable material.

4. The method according to claim 1, further comprising, after step
   a), a step for deactivating the endogenous enzymes of the water/vegetable material mixture.

5. The method according to claim 1, wherein the enzyme mixture contains the enzyme activities in the following proportions:
   cellulases:
      betaglucosidase: between 1 µmol/min/mL and 30 µmol/min/mL,
      endocellulase: between 20 µmol/min/mL and 200 µmol/min/mL,
      exocellulase : between 0 and 50 µmol/min/mL,
   hemicellulases:
      arabinanase : between 300 µmol/min/mL and 2,000 µmol/min/mL,
      xylanase : between 0 and 2,000 µmol/min/mL,
      galactanase: between 300 µmol/min/mL and 2,000 µmol/min/mL, and
   pectinases:
      endopolygalacturonase: between 40 µmol/min/mL and 120 µmol/min/mL, pectin methylesterase: between 1 µmol/min/mL and 20 µmol/min/mL.

6. The method according to claim 1, wherein the enzyme mixture further comprises a phenolic acid esterase, the activity of which is between 1 µmol/min/mL and 15 µmol/min/mL.

7. The method according to claim 6, wherein the phenolic acid esterase is ferulic acid esterase.

8. The method according to claim 1, wherein the amount of the enzyme mixture is between 0.25% and 10% by volume of the water/vegetable material mixture.

9. The method according to claim 1, wherein the incubation according to step c) is carried out for 2 to 20 hours, at a temperature between 25° C. and 75° C.

10. The method according to claim 1, wherein the stirring provided in step c) is achieved by means of a mixer comprising flat blades promoting mixing and limiting shear.

11. The method according to claim 1, wherein no step for correcting the pH is provided.

12. The method according to claim 1, wherein the separation step d) is achieved by means of a tricanter.

13. The method according to claim 1, wherein the vegetable material is selected from the group consisting of fat cakes from the first pressing and oilseeds.

14. The method according to claim 13, wherein the oilseeds are selected from the group consisting of rapeseed and sunflower.

15. A method for suppressing any step for correcting the pH in an enzyme method for extracting in an aqueous medium, oils, proteins and fermentable sugars from vegetable material, comprising a step of adding to the vegetable material an enzyme mixture containing at least one cellulase, at least one hemicellulase, and at least one pectinase, the ratio between the pectinase activity and the cellulase activity being at least 0.14, the ratio between the pectinase activity and the hemicellulose activity being between $1 \times 10^{-2}$ and 0.5, and the pectinase activity being less than 120 µmol/min/mL.

16. The method according to claim 15, wherein the enzyme mixture contains the enzyme activities in the following proportions:
cellulases:
betaglucosidase: between 1 µmol/min/mL and 30 µmol/min/mL,
endocellulase: between 20 µmol/min/mL and 200 µmol/min/mL,
exocellulase: between 0 and 50 µmol/min/mL,
hemicellulases:
arabinanase: between 300 µmol/min/mL and 2,000 µmol/min/mL,
xylanase: between 0 and 2,000 µmol/min/mL,
galactanase: between 300 µmol/min/mL and 2,000 µmol/min/mL,
pectinases:
endopolygalacturonase: between 40 µmol/min/mL and 120 µmol/min/mL,
pectin methylesterase: between 1 µmol/min/mL and 20 µmol/min/mL.

\* \* \* \* \*